US005241925A

United States Patent [19]

Gertner et al.

[11] Patent Number: 5,241,925

[45] Date of Patent: Sep. 7, 1993

[54] APPARATUS AND TECHNIQUES FOR ADMINISTERING VETERINARY MEDICAMENTS

[75] Inventors: Avi Gertner, Kfar Saba; Yosef Rubinstein, Nes Ziona, both of Israel

[73] Assignee: Dermamed, Ness Ziona, Israel

[21] Appl. No.: 727,217

[22] Filed: Jul. 9, 1991

Related U.S. Application Data

[62] Division of Ser. No. 451,679, Dec. 18, 1989, Pat. No. 5,049,143.

[30] Foreign Application Priority Data

Dec. 27, 1988 [IL] Israel ........................................ 88808

[51] Int. Cl.$^5$ .......................... A61F 13/00; F22B 7/00

[52] U.S. Cl. .................................... 119/156; 119/174; 604/308; 604/304

[58] Field of Search ................ 119/156, 174; 604/304, 604/308, 289; 424/448, 419; 514/14

[56] References Cited

U.S. PATENT DOCUMENTS

| | | | |
|---|---|---|---|
| 3,942,480 | 3/1976 | Hair et al. . | |
| 3,970,080 | 7/1976 | White . | |
| 3,996,934 | 12/1976 | Zaffaroni . | |
| 4,026,290 | 5/1977 | Brooker et al. . | |
| 4,221,189 | 9/1980 | Olvera . | |
| 4,428,327 | 1/1984 | Steckel . | |
| 4,435,180 | 3/1984 | Leeper . | |
| 4,486,194 | 12/1984 | Ferrara . | |
| 4,506,630 | 3/1985 | Hair . | |
| 4,585,797 | 4/1986 | Cioca . | |
| 4,588,580 | 5/1986 | Gale et al. | 604/304 |
| 4,620,849 | 11/1986 | Corner . | |
| 4,638,043 | 1/1987 | Szycher et al. . | |
| 4,666,441 | 5/1987 | Andriola et al. | 504/304 |
| 4,673,665 | 6/1987 | Humke | 514/14 |
| 4,694,781 | 9/1987 | Howe et al. | 119/156 |
| 4,725,279 | 2/1988 | Woodroof . | |
| 4,767,402 | 8/1988 | Kost et al. . | |
| 4,775,372 | 10/1988 | Wilberg . | |
| 4,777,047 | 10/1988 | Bauer et al. . | |
| 4,792,450 | 9/1988 | Kydonieus et al. . | |
| 4,818,540 | 4/1989 | Chien et al. . | |
| 4,820,525 | 4/1989 | Leonard et al. . | |
| 4,822,617 | 4/1989 | Panoz . | |
| 4,879,297 | 11/1989 | Mahjour et al. . | |
| 4,908,389 | 3/1990 | Mahjour et al. . | |
| 4,930,451 | 6/1990 | Miller et al. . | |
| 4,952,402 | 8/1990 | Sparks et al. | 424/419 |
| 5,028,435 | 7/1991 | Katz et al. | 424/448 |
| 5,059,427 | 10/1991 | Yoshida et al. . | |

FOREIGN PATENT DOCUMENTS

| | | |
|---|---|---|
| 28462/77 | 3/1979 | Australia . |
| 66647/81 | 8/1981 | Australia . |
| 79545/82 | 8/1982 | Australia . |
| 79212/82 | 1/1983 | Australia . |
| 31850/84 | 2/1985 | Australia . |
| 39352/85 | 5/1986 | Australia . |
| 60222/86 | 9/1987 | Australia . |
| 166990 | 1/1974 | New Zealand . |
| 178922 | 12/1977 | New Zealand . |
| 179341 | 12/1977 | New Zealand . |
| 200232 | 8/1985 | New Zealand . |
| 206173 | 4/1986 | New Zealand . |

(List continued on next page.)

OTHER PUBLICATIONS

Pitman, I. H., et al, "Topical Drug Delivery to Cattle and Sheep", Jour. of Pharm. Sci., vol. 70, No. 11, Nov., 1981, pp. 1181-1193.

Pitman, I. H., et al, "A Comparison of Frozen and Reconstituted Cattle and Human Skin as Barriers . . . ", Jour. of Pharm. Sci., vol. 71, No. 4, Apr., 1982, pp. 427-430.

*Primary Examiner*—John G. Weiss
*Attorney, Agent, or Firm*—Browdy and Neimark

[57] ABSTRACT

A technique for administering medicaments in veterinary applications including the steps of applying a medicament transdermally to an animal and non-surgically terminating the application of the medicament at a predetermined time. There is also provided apparatus for transdermal application of medicaments to animals including a removable enclosure arranged to be non-invasively mounted onto an animal ear.

8 Claims, 12 Drawing Sheets

FOREIGN PATENT DOCUMENTS

| | | |
|---|---|---|
| 204870 | 6/1986 | New Zealand . |
| 207874 | 1/1987 | New Zealand . |
| 208597 | 2/1987 | New Zealand . |
| 209843 | 3/1987 | New Zealand . |
| 210356 | 4/1987 | New Zealand . |
| 208692 | 3/1988 | New Zealand . |
| 210689 | 8/1988 | New Zealand . |
| 214496 | 3/1989 | New Zealand . |
| 215746 | 8/1989 | New Zealand . |
| 222761 | 10/1989 | New Zealand . |
| 221991 | 12/1989 | New Zealand . |
| 225907 | 5/1990 | New Zealand . |
| 224682 | 6/1990 | New Zealand . |
| 224707 | 9/1990 | New Zealand . |
| 228637 | 10/1990 | New Zealand . |
| 228562 | 5/1991 | New Zealand . |
| 226209 | 6/1991 | New Zealand . |
| 231907 | 10/1991 | New Zealand . |
| 231908 | 10/1991 | New Zealand . |
| 228533 | 1/1992 | New Zealand . |
| 1515925 | 6/1978 | United Kingdom . |
| 1519149 | 7/1978 | United Kingdom . |
| 87/04936 | 8/1987 | World Int. Prop. O. . |

FIG.1A
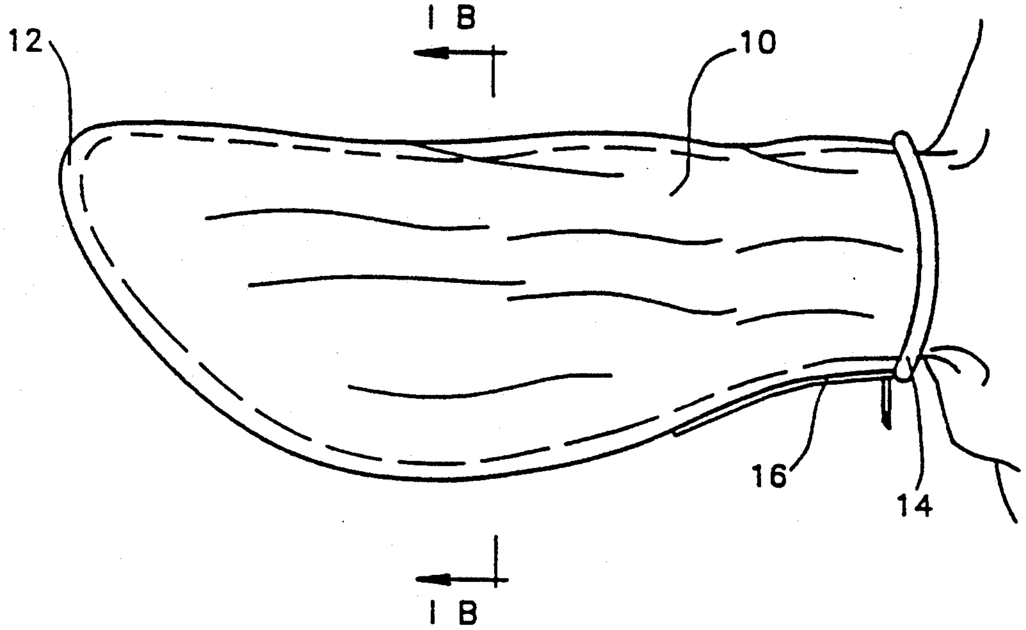
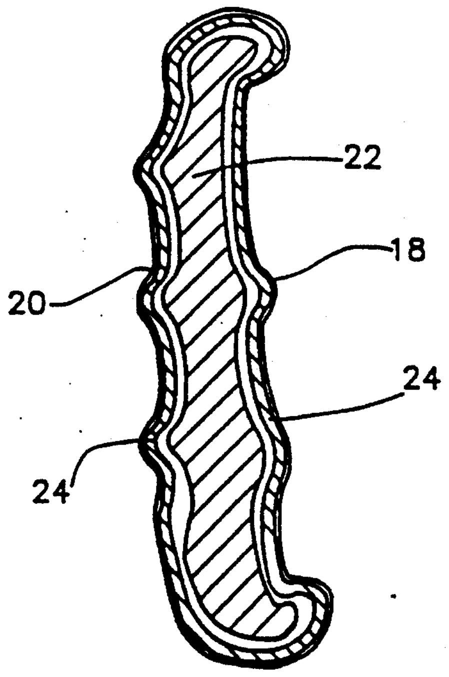
FIG.1B

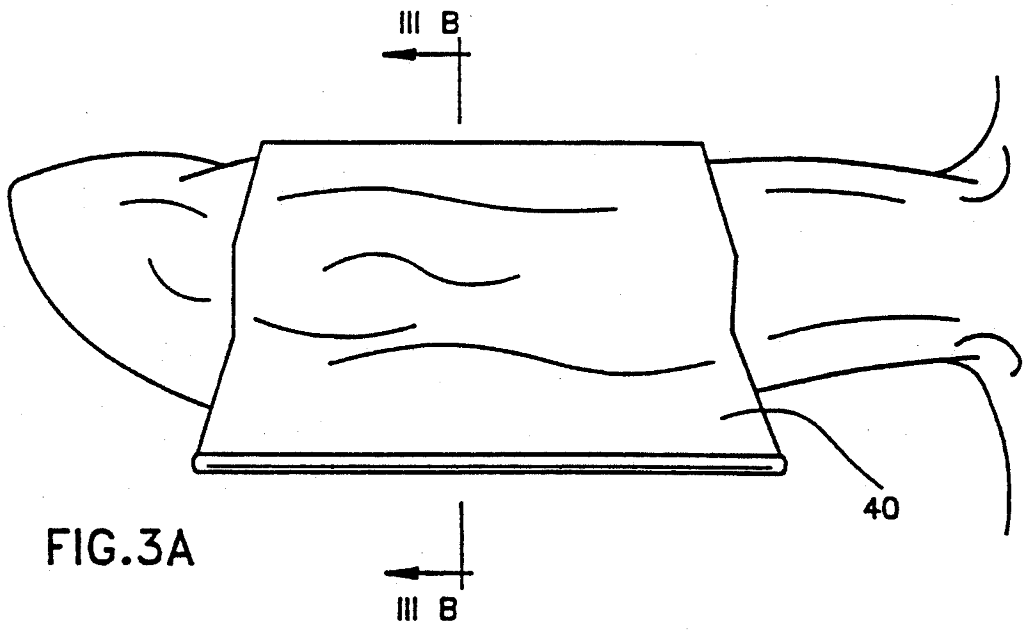
FIG.3A
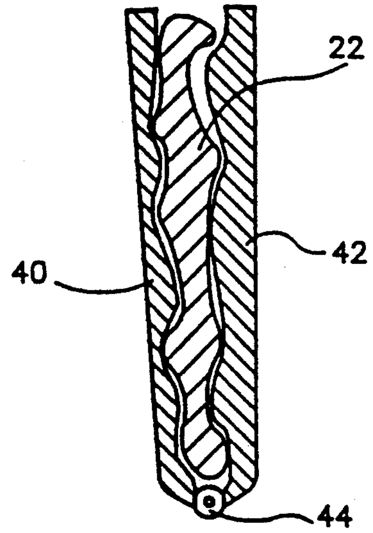
FIG.3B
FIG.4
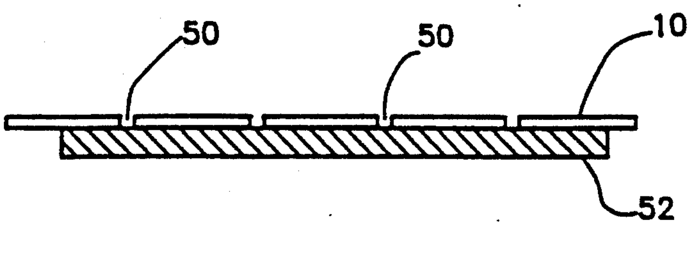

APPARATUS AND TECHNIQUES FOR ADMINISTERING VETERINARY MEDICAMENTS

This application is a divisional of application Ser. No. 07/451,679 filed on Dec. 18, 1989, now U.S. Pat. No. 5,049,143.

FIELD OF THE INVENTION

The present invention relates generally to animal husbandry and more particularly to apparatus and techniques for administering veterinary medicaments through the skin.

BACKGROUND OF THE INVENTION

Various techniques and devices are known for administering medicaments through the skin, particularly for veterinary use. One example of such a technique is described in U.S. Pat. No. 4,026,290, which suggests attachment of a device to the ears or tail of the animal for applying motion sickness mitigators, anti-migraine compounds, analgesics, anthelmintics, antiprotozoal compounds and systemic insecticides, miticide and acaricides.

Transdermal drug delivery in veterinary applications is discussed in an article entitled "Topical Drug Delivery to Cattle and Sheep" by Ian H. Pitman and Susan J. Rostas, in Journal of Pharmaceutical Sciences, Vol. 70, No. 11, November, 1981, pp. 1181-1193 and in an article by the same authors entitled "A Comparison of Frozen and Reconstituted Cattle and Human Skin as Barriers to Drug Penetration", in Journal of Pharmaceutical Sciences, Vol. 71, No. 4, April, 1982, pp 427-430. Transdermal drug delivery has been proposed for administering prophylactic medicaments in veterinary contexts but, to the best of the knowledge of the inventors, has not had any practical application of significance in veterinary practice.

Growth regulators and growth promoters, here collectively termed "growth promoters", are commonly used in veterinary applications and are often applied using implants which cannot be conveniently removed prior to slaughter. Hormones for synchronization in mammals are generally administered vaginally, a technique which requires skill and involves potential damage to the animal and could result in infertility.

SUMMARY OF THE INVENTION

The present invention seeks to provide techniques and apparatus for veterinary transdermal application of medicaments.

There is thus provided in accordance with a preferred embodiment of the present invention a technique for administering medicaments in veterinary applications comprising the steps of applying a medicament transdermally to an animal and non-surgically terminating the application of the medicament at a pre-determined time.

The termination of the application of the medicament may be precisely timed so as to prevent residues of the medicament from remaining in the tissues of the animal or in food products produced thereby, such as milk.

Additionally in accordance with a preferred embodiment of the present invention, the step of non-surgically terminating the application of the medicament takes place at least a pre-determined length of time before slaughter of the animal for preventing more than a predetermined threshold of the residue of the medicament from remaining in the slaughtered animal.

The medicaments may be any suitable medicament and may include, for example, growth promoters, fertility agents, medicaments for the control of ovulation in breeding animals, nutritional supplements such as vitamins and trace elements.

Alternatively in accordance with a preferred embodiment of the invention the medicament is an agent for the control of ovulation in breeding animals and the steps of applying and non-surgically terminating application of the medicament occur at preselected times which are synchronized for a herd.

Additionally in accordance with a preferred embodiment of the invention there is provided apparatus for transdermal application of medicaments to animals comprising a removable enclosure arranged to be non-invasively mounted onto an animal ear.

In accordance with one embodiment of the invention, the enclosure comprises a glove-like enclosure arranged to fit over the ear and having a selectable closure associated therewith.

The selectable closure may comprise, for example, a zip fastener, or an arrangement of clips or other fasteners which engage each other peripherally of the ear.

According to an alternative embodiment of the invention, the removable enclosure may comprise a pair of planar members which are urged together in engagement by a resilient device.

In accordance with a preferred embodiment of the invention, the removable enclosure is arranged to apply medicaments to two opposite surfaces of the ear. Alternatively a medicament may be applied on only one of the opposite surfaces. As further alternatives, more than one medicament may be applied on a given surface or two or more different medicaments may be applied on different surfaces of the enclosure. As yet a further alternative, different medicaments may be applied to different ears of the animal.

It is a particular feature of the present invention that no aseptic or other preparation of the animal is required prior to application of the medicament, inasmuch as the enclosure may be mounted on an unprepared and untreated ear.

In accordance with a preferred embodiment of the invention, the removable enclosure is arranged such that in normal application and use, the medicament does not come into physical contact with a person applying or removing the enclosure.

In accordance with one embodiment of the invention, the inner surfaces of the enclosure may be impregnated with a desired medicament. Alternatively, a separate medicament support element may be provided interior of the enclosure.

In accordance with a preferred embodiment of the invention, the medicament may be configured to provide a desired controlled or sustained release pattern.

It is a particular feature of the invention that the removable enclosure provides a visual indication of which animals are being treated. Suitable color or pattern coding may be provided on the enclosure to indicate the type and/or duration of treatment.

In accordance with a preferred embodiment of the invention, the medicament is a growth promoter. In accordance with another preferred embodiment of the invention, the medicament is a fertility drug. In accordance with yet another preferred embodiment of the invention, the medicament is a fertility synchronization agent. Additionally in accordance with another preferred embodiment of the invention, the medicament is a nutritional supplement. Alternatively in accordance with another preferred embodiment of the invention, the medicament is an anti-inflammatory agent.

BRIEF DESCRIPTION OF THE DRAWINGS

The present invention will be understood and appreciated more fully from the following detailed description taken together with the drawings in which:

FIGS. 1A and 1B are respective pictorial and sectional illustrations of a removable enclosure for transdermal application of medicaments to the ear of an animal in accordance with a preferred embodiment of the present invention;

FIGS. 3A and 3B are respective pictorial and sectional illustrations of a removable enclosure for transdermal application of medicaments to the ear of an animal in accordance with yet another preferred embodiment of the present invention;

FIG. 4 is an enlarged sectional illustration of part of the enclosure of any of FIGS. 1A-3B;

DETAILED DESCRIPTION OF PREFERRED EMBODIMENTS

Figure 2A:
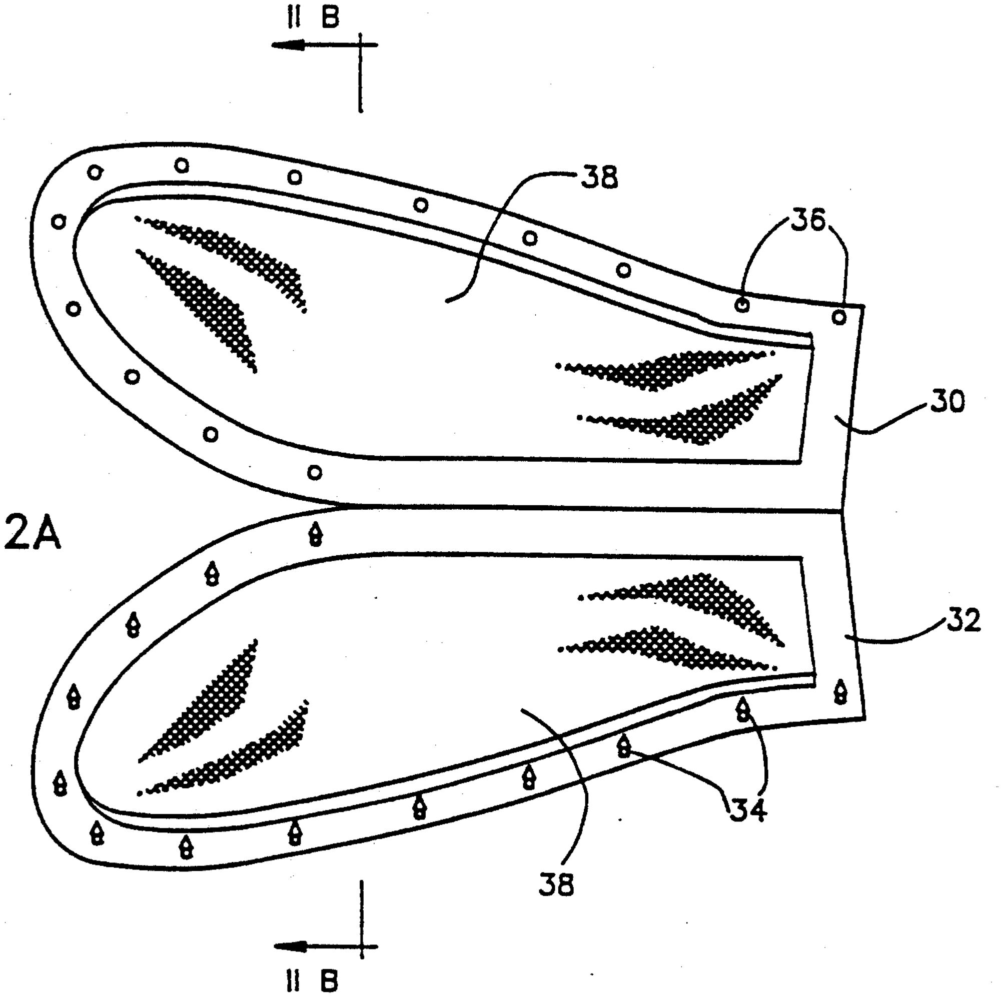
FIGS. 2A and 2B are respective pictorial and sectional illustrations of a removable enclosure for transdermal application of medicaments to the ear of an animal in accordance with another preferred embodiment of the present invention, FIG. 2A illustrating the enclosure in an opened orientation, and FIG. 2B, illustrating the enclosure in a closed orientation.

Reference is now made to FIGS. 1A and 1B which illustrate one embodiment of the invention Wherein a removable enclosure 10 is provided for fitting over the ear of the animal. The enclosure 10 may typically be formed in the general configuration of a sleeve having a closed outer end 12 and an open inner end 14. Adjacent the inner end 14 there is provided a fastener 16, such as a zipper or any other type of suitable fastener such as snaps, for retaining the enclosure 10 on the ear of an animal.

According to a preferred embodiment of the invention, the enclosure 10 defines two generally planar surfaces 18 and 20 which contact the respective facing planar surfaces of the ear 22 of the animal. According to one embodiment of the invention, as illustrated, there is provided a layer 24 of medicament bearing material, such as cotton wool, gauze, a gel, or any other suitable type of support matrix. According to an alternative embodiment of the invention, the medicament may be directly impregnated into the material of the enclosure 10, which may be a plastic or partially plastic material such as a thermoplastic material, for example, PVC, Nylon, Polypropylene, Polyethylene and Vinyl. It has been found to be desirable that the both the enclosure and the layer 24, if provided, be configured to allow good exposure of the animal skin to the air, to prevent undesired inflammation of the skin under the enclosure and in contact with the medicament.

Figure 2B:
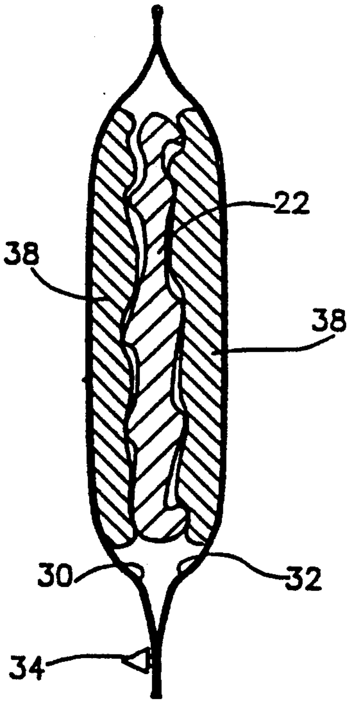
Figure 5:
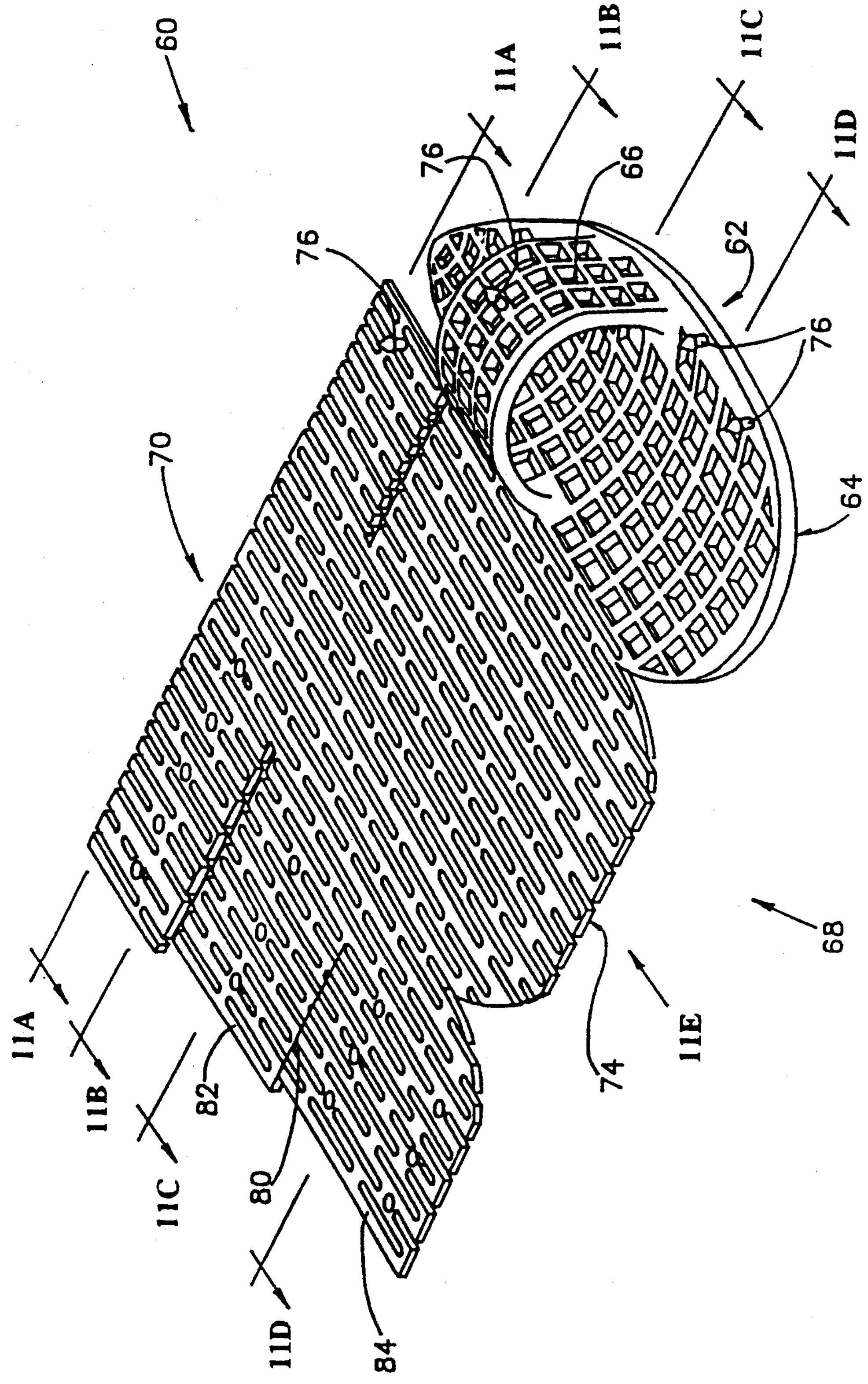
FIGS. 5 and 6 are pictorial illustrations of the front and back respectively of apparatus for applying a medicament transdermally to an animal ear constructed and operative in accordance with a preferred embodiment of the present invention.
Figure 6:
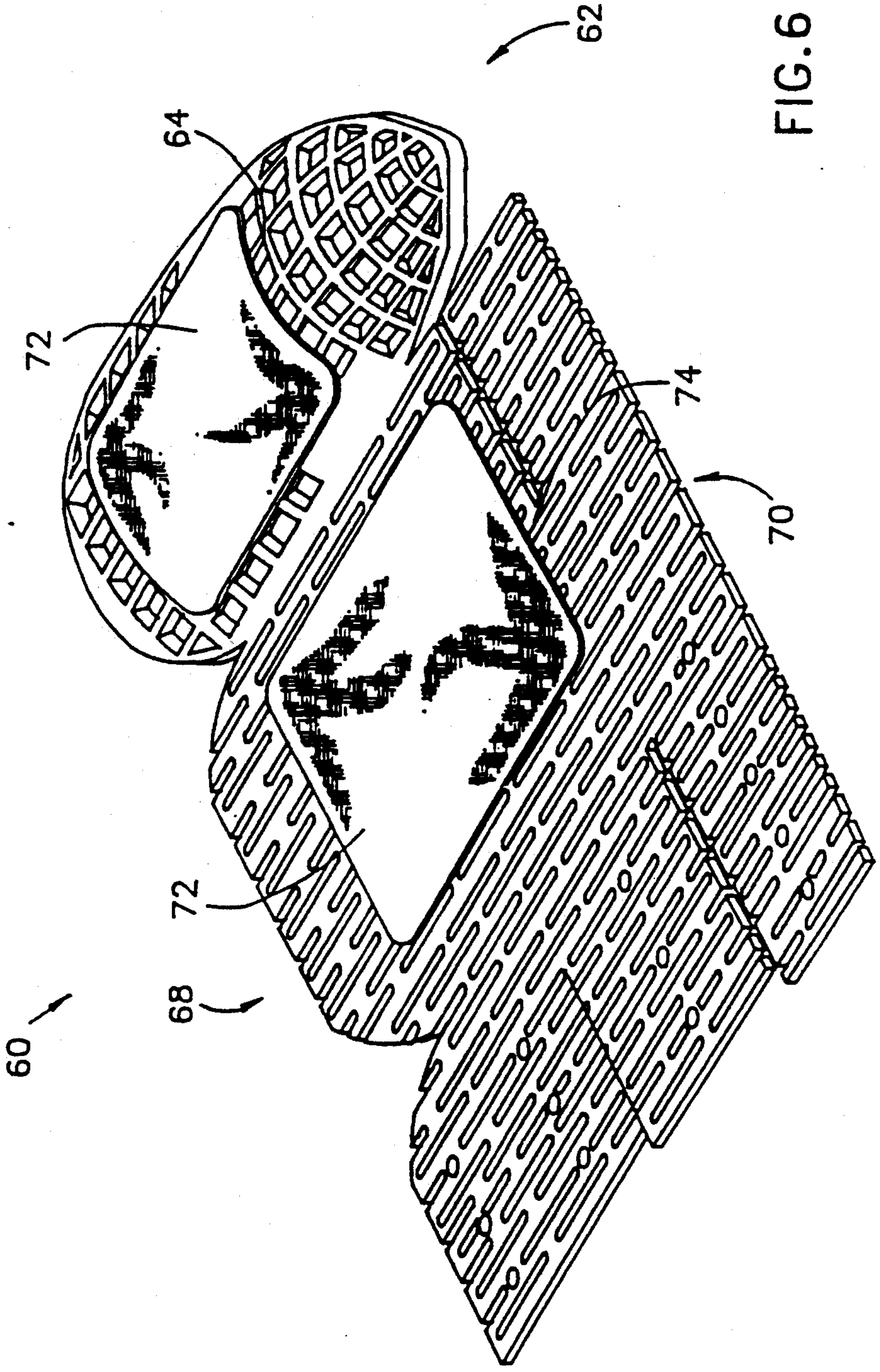

Reference is now made to FIGS. 2A and 2B which illustrate an alternative embodiment of enclosure 10. Here, the enclosure comprises two joined leaves 30 and 32 having associated fasteners 34 which engage apertures 36. A medicament containing pad, patch or support matrix 38 is typically associated with each of leaves 30 and 32. Alternatively, one or more medicaments may be impregnated directly into leaves 30 and 32. In a preferred embodiment of the invention, the pad should be "breathable" or alternatively be formed of a plurality of small pads which are separated so as to allow air access therebetween.

Reference is now made to FIGS. 3A and 3B, which illustrate yet another alternative embodiment of the invention wherein the enclosure is not a closed enclosure but rather comprises two leaves 40 and 42 which are arranged in a folded orientation surrounding a portion of an animal ear 22. The two leaves 40 and 42 are typically urged towards each other, thus grasping the ear 22, by means of a conventional coil spring mechanism 44.

As in the earlier described embodiments, a medicament may be impregnated directly into leaves 40 and 42 or alternatively medicament containing pads or other support matrices may be provided. In a preferred embodiment of the invention, the pad should be "breathable" or alternatively be formed of a plurality of small pads which are separated so as to allow air access therebetween.

Reference is now made to FIG. 4, which shows a detail of a portion of the enclosure 10 having pores 50 which communicate either directly between the atmosphere and the animal ear or, as shown, via a porous medicament support pad 52. The provision of pores is applicable equally to all of the embodiments illustrated in FIGS. 1A-3B. In a preferred embodiment of the invention, the pad should be "breathable" or alternatively be formed of a plurality of small pads which are separated so as to allow air access therebetween.

It will be appreciated that all of the illustrated embodiments are only some examples of enclosures which may be employed in accordance with a preferred embodiment of the invention. The enclosure may be designed for a single use and thus be disposable or may be employed for multiple use.

The enclosures may be color or pattern encoded to provide a ready means of identification of the type and duration of treatment to the animal husbandry operative.

There is also provided in accordance with a preferred embodiment of the present invention a technique for administering medicaments in veterinary applications comprising the steps of applying a medicament transdermally to an animal and non-surgically terminating the application of the medicament at a pre-determined time.

The termination of the application of the medicament may be precisely timed so as to prevent residues of the medicament from remaining in the tissues of the animal or in food products produced thereby, such as milk.

Additionally in accordance with a preferred embodiment of the present invention, the step of non-surgically terminating the application of the medicament takes place at least a pre-determined length of time before slaughter of the animal for preventing more than a pre-determined threshold of the residue of the medicament from remaining in the slaughtered animal. The medicaments may be any suitable medicament and may include, for example, growth promoters, fertility agents, medicaments for the control of ovulation in breeding animals, nutritional supplements such as vitamins and trace elements, and anti-inflammatory agents.

Alternatively in accordance with a preferred embodiment of the invention the medicament is an agent for the control of ovulation in breeding animals and the steps of applying and non-surgically terminating application of the medicament occur at preselected times which are synchronized for a herd.

An example of the use of the invention in fertility synchronization is application of progesterone to ewes for 13 consecutive days by attachment of an enclosure as described above to the ewe's ear. Following the prescribed 13 days, the enclosure is removed and discarded. Mating should occur within 24 hours thereafter. Slaughter of the animal in any case should not take place less than 48 hours following removal of the enclosure.

An example of the use of the invention in the application of growth promoters is application of a combination of estradiol and progesterone to male cattle for 90 consecutive days by attachment of an enclosure as described above to the steer's ear. Following the prescribed 90 days, the enclosure is removed and discarded. Slaughter of the animal may take place no less than 5 days following removal of the enclosure.

An example of the use of the invention in the application of nutritional supplements such as vitamins and trace elements is application of selenium to cows for 90 consecutive days by attachment of an enclosure as described above to the cow's ear. Following the prescribed 90 days, the enclosure is removed and discarded. Application of the enclosure should be carried out at least 8 weeks before calving and terminated at the end of the weaning period.

In accordance with a preferred embodiment of the invention, the removable enclosure and the medicament pad are arranged such that in normal application and use, the medicament does not come into physical contact with a person applying or removing the enclosure.

Reference is now made to FIGS. 5–8 and 11A–11E, which illustrate the structure and mounting of a removable medicament-bearing enclosure constructed and operative in accordance with a preferred embodiment of the invention. The enclosure, indicated generally by reference numeral 60, comprises an inner ear portion 62 typically formed of a perforate web material of plastic, metal or any other suitable material.

The inner ear portion 62, serves to support the ear against deformation and includes a medicament supporting curved portion 64, which lies against the inner surface of the animal ear and a bridge member 66 which supports the desired curvature of portion 64 and maintains spacing of the enclosure as desired.

Associated with inner ear portion 62 and preferably integrally formed therewith is an outer ear wrap portion 68 and a collar portion 70. Preferably the inner ear portion 62 is formed of material which is somewhat more rigid than the material used for the outer ear wrap portion 68 and the collar portion 70.

The outer ear portion 68 is typically formed of a perforate web material of plastic, metal or any other suitable material which is somewhat stretchable. The collar portion 70 may be formed of identical material but should have limited stretchability.

As noted above in earlier described embodiments, the medicament may be impregnated in the enclosure material or alternatively and preferably the medicament is provided on pads or patches 72 mounted on surface 64 of the inner ear engaging portion 62 and on surface 74 of outer ear wrap. In a preferred embodiment of the invention, the pad or patch should be "breathable" or alternatively be formed of a plurality of small pads which are separated so as to allow air access therebetween.

Figure 7:
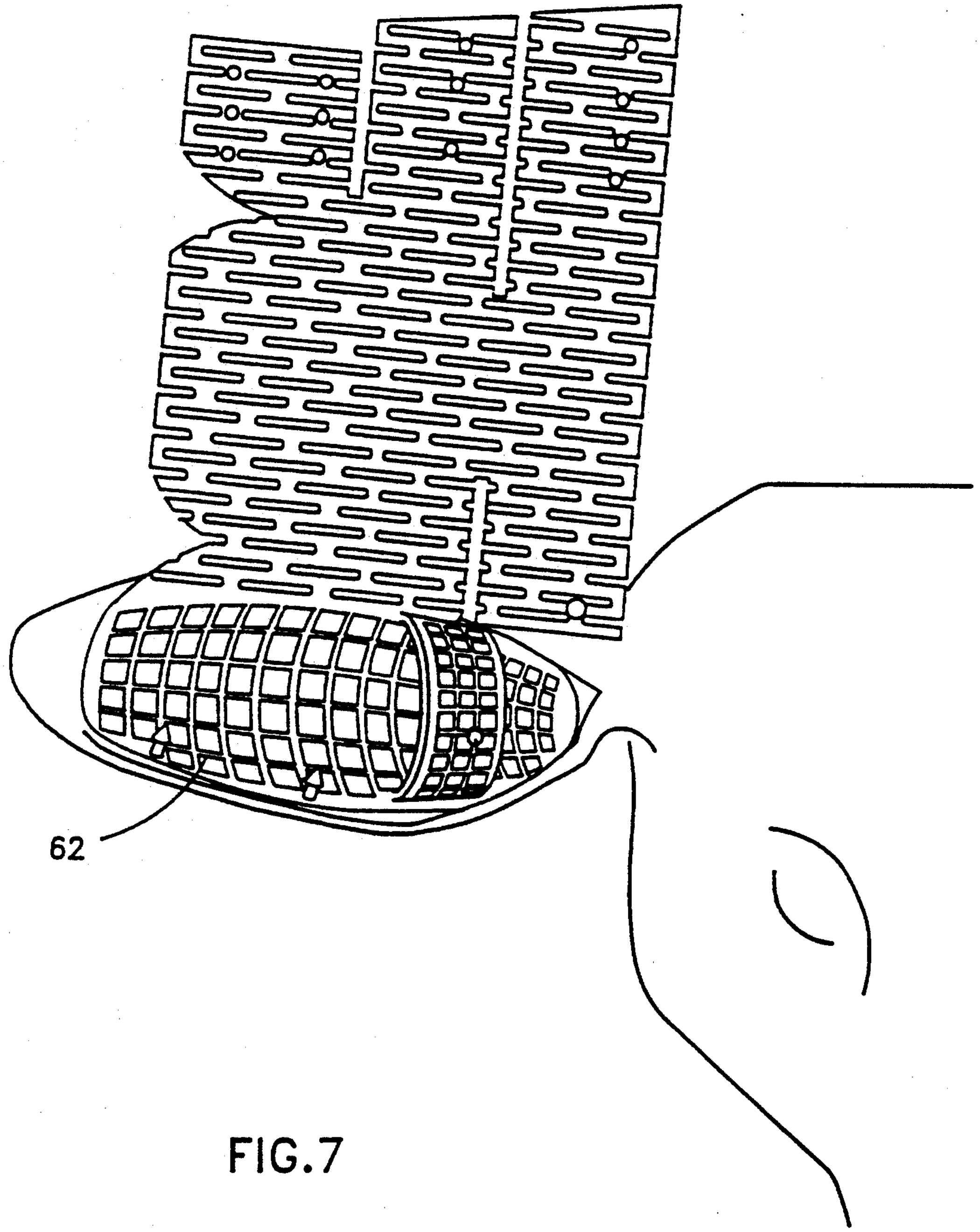
FIG. 7 is a pictorial illustration of the apparatus of FIGS. 5 and 6 partially mounted onto the ear of an animal.
Figure 8:
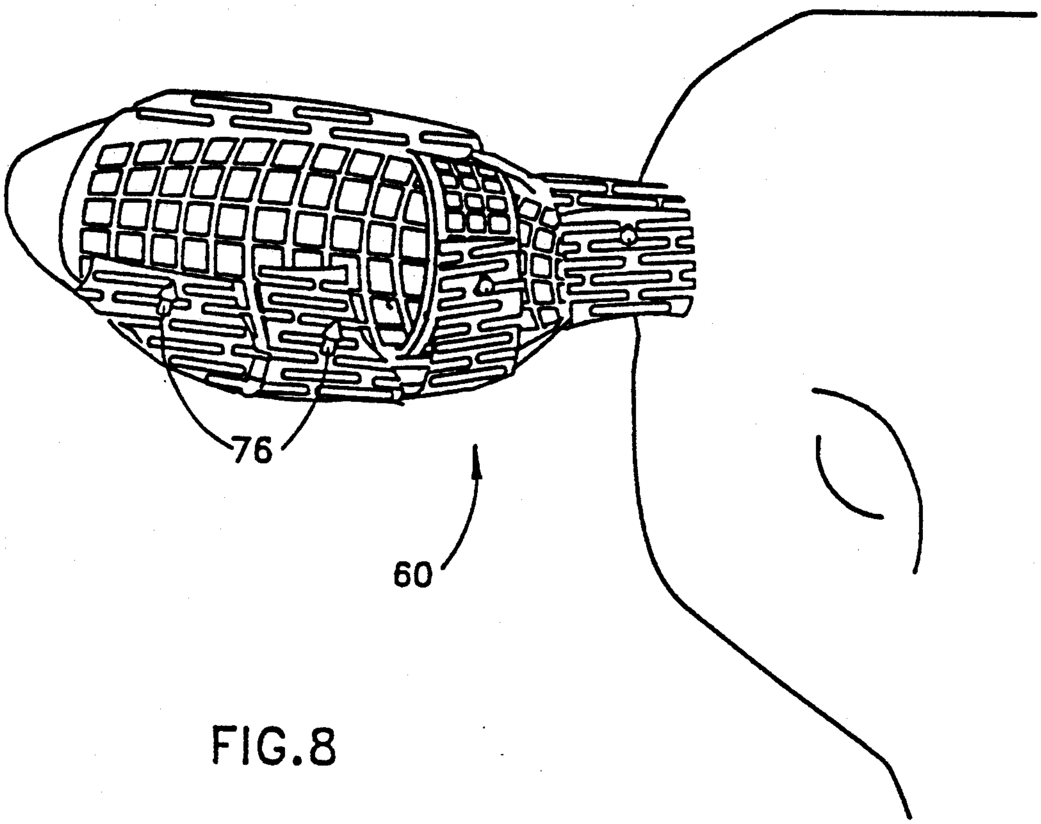
FIG. 8 is a pictorial illustration of the apparatus of FIGS. 5 and 6 fully mounted onto the ear of an animal.

FIG. 7 illustrates initial insertion of the inner ear engaging portion 62 into the ear of an animal and FIG. 8 illustrates complete fastening of the enclosure 60 onto the animal ear. It is noted that the collar portion is adjustably fastened relatively tightly about the narrow part of the ear closest to the head of the animal, in order to retain the enclosure on the ear. When it is desired to remove the enclosure, it is usually sufficient to unfasten the collar portion and to slide the enclosure off the ear.

In the illustrated embodiment, bayonet type fasteners 76 are employed, it being understood that any suitable type of fasteners may be employed. It is appreciated that in the illustrations the enclosure for a right ear is shown. The enclosure for the left ear is configured correspondingly.

It is noted that the fastening arrangement on the outer ear wrap portion is such that various differently sized ears may be readily accomodated by a universal enclosure. Different sized enclosures may however be required for full grown cows and calves, for example.

In the illustrated embodiment, the outer ear wrap portion includes a slit 80 between adjacent strap portions 82 and 84, in order to accomodate the curvature of the ear. Depending on the construction of the enclosure, this slit may be eliminated.

Figure 12:
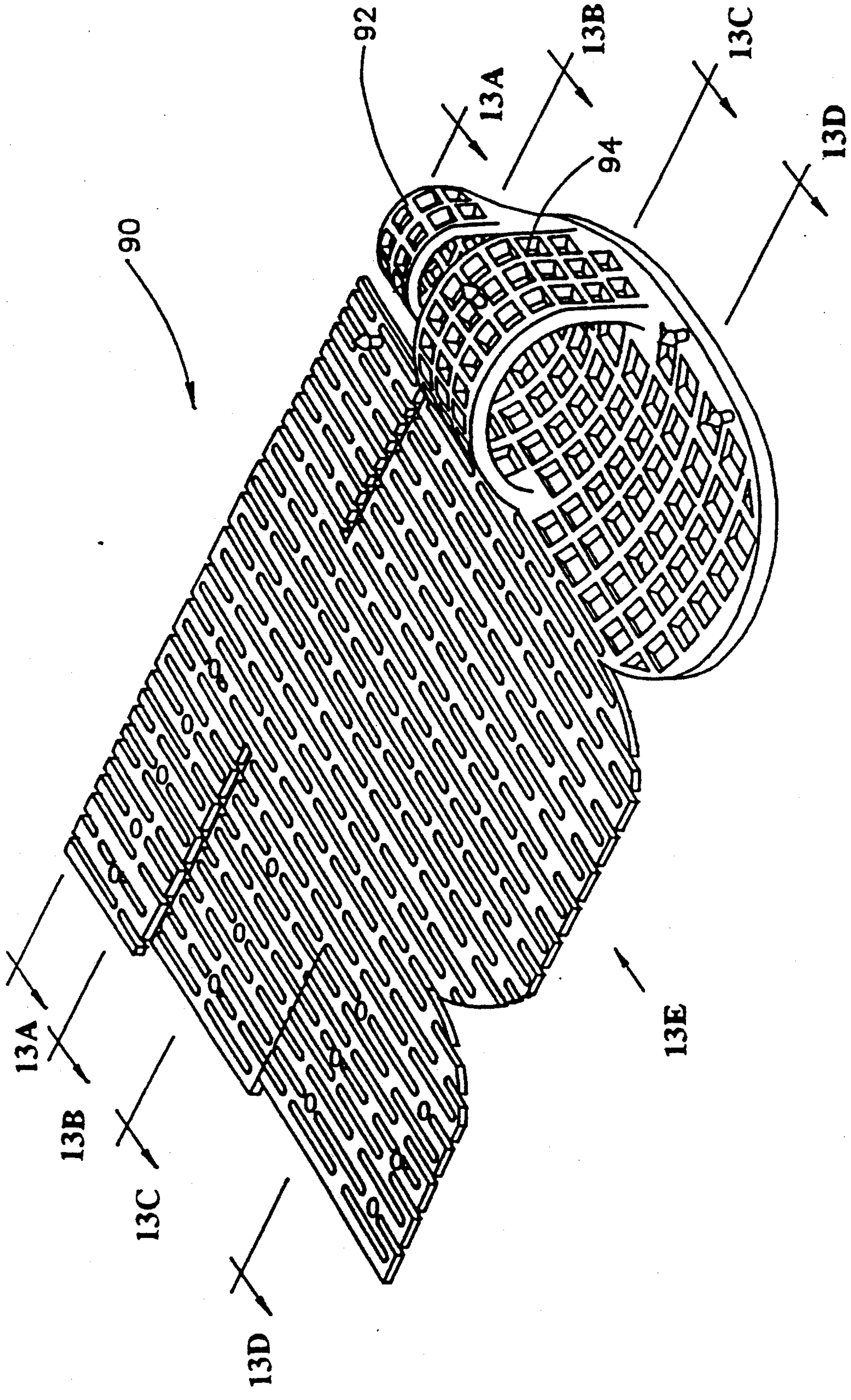
FIG. 12 is a pictorial illustration of the front of apparatus for applying a medicament transdermally to an animal ear constructed and operative in accordance with another preferred embodiment of the present invention.
Figures 13A, 13B, 13C, 13D, 13E:
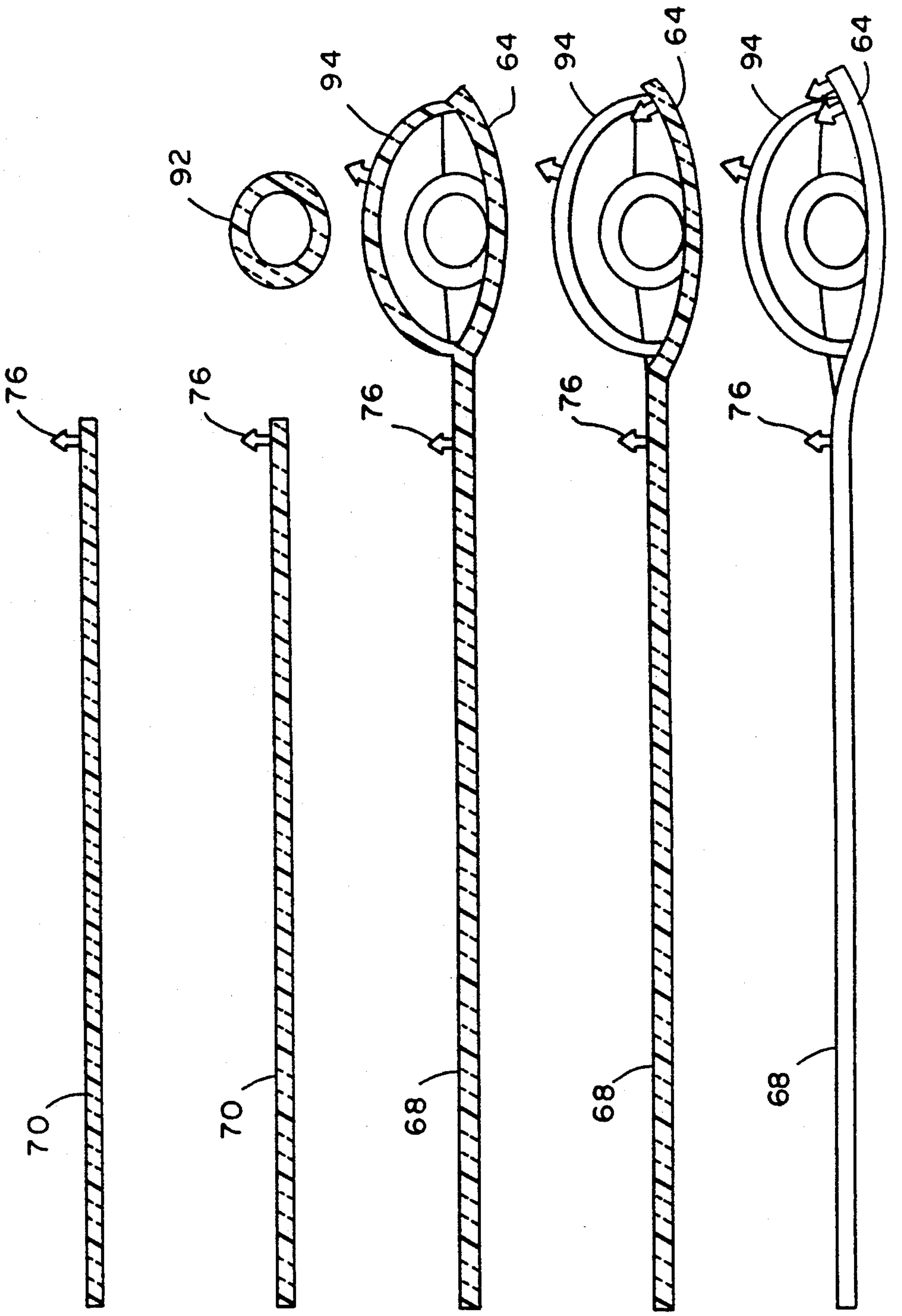
FIGS. 13A, 13B, 13C, 13D and 13E are sectional illustrations taken along lines 13A—13A, 13B—13B, 13C—13C, 13D—13D in the direction 13E in FIG. 12.

An alternative embodiment of an enclosure, particularly suitable for use with sheep, goats and other small animals, is illustrated in FIG. 12. It is noted that enclosure 90 includes two bridge members 92 and 94 for enhanced support of the ear.

EXAMPLE I

Figure 9:
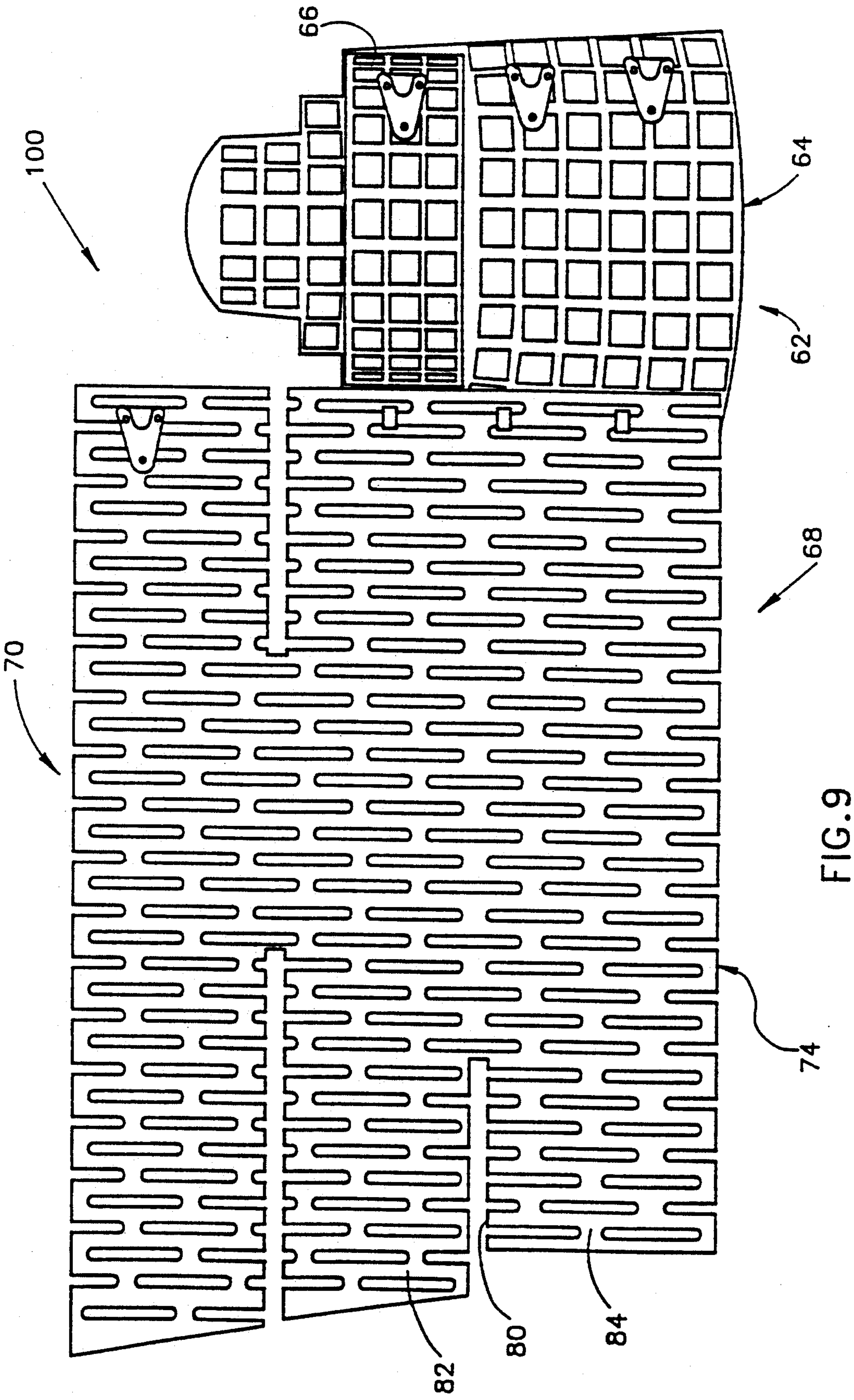
FIGS. 9 and 10 are pictorial illustrations of the front and back respectively of experimental apparatus for applying a medicament transdermally to an animal ear employed in the Examples set forth hereinbelow.
Figure 10:
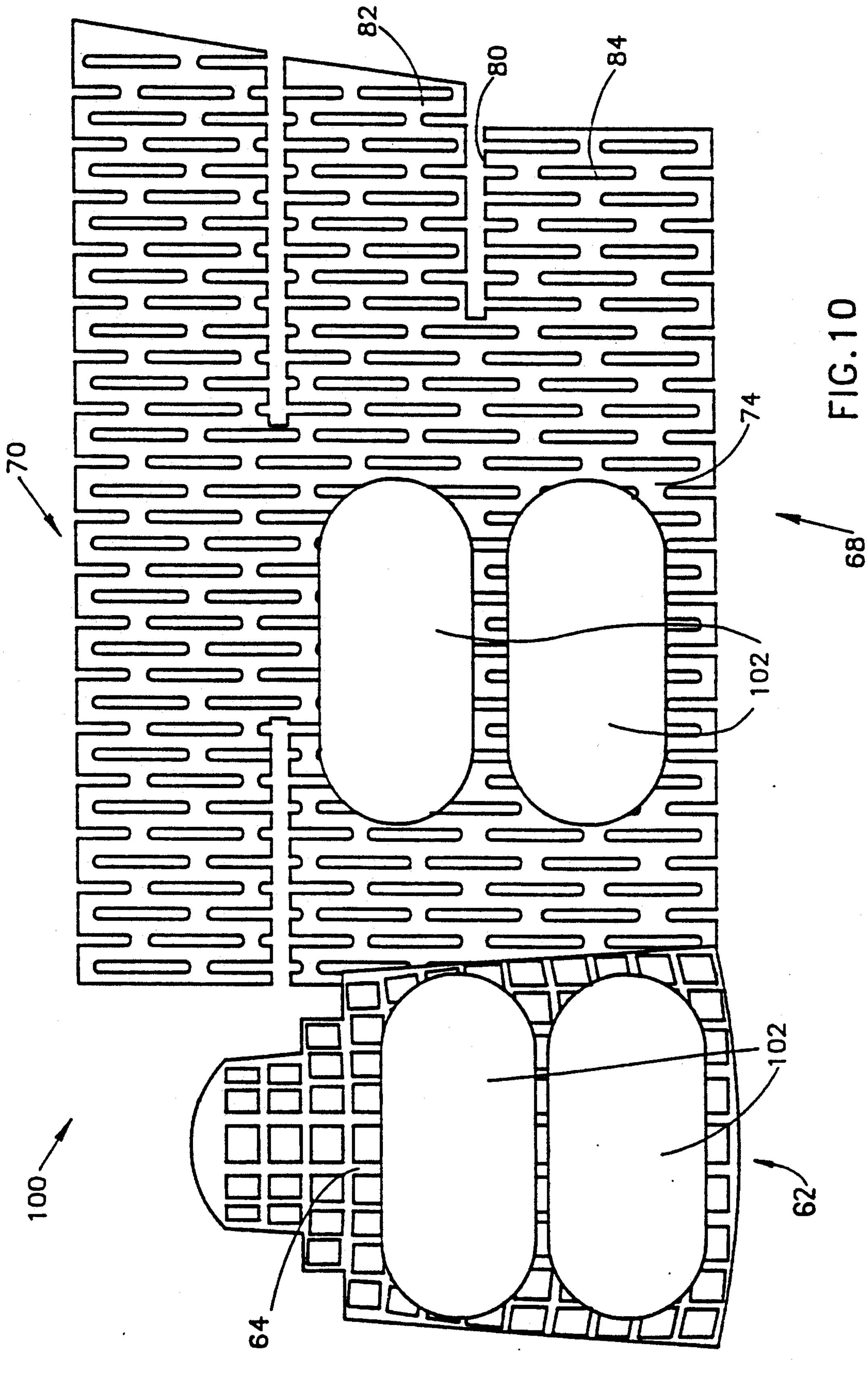
Figures 11A, 11B, 11C, 11D, 11E:
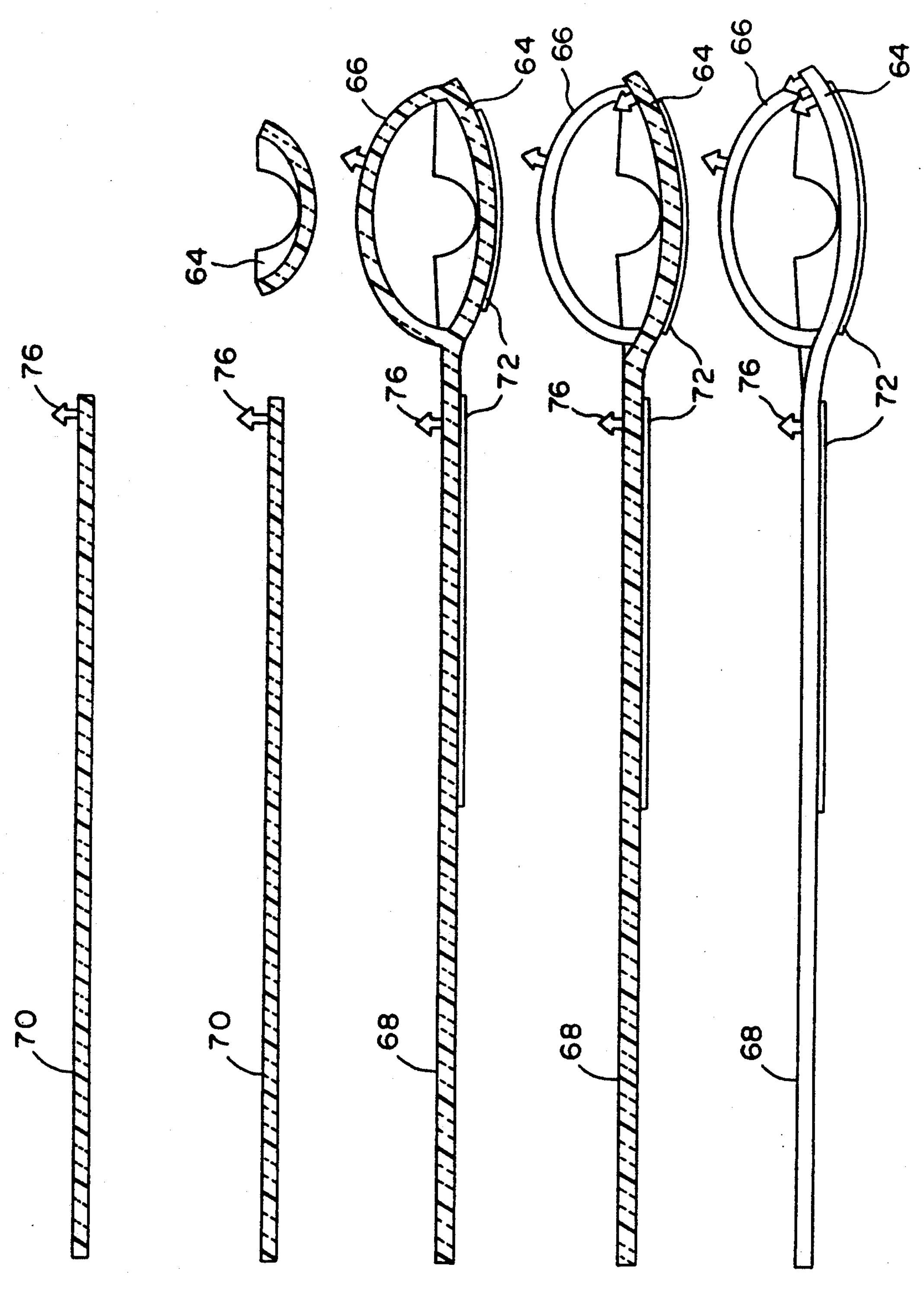
FIGS. 11A, 11B, 11C, 11D and 11E are illustrations taken along lines 11A—11A, 11B—11B, 11C—11C, 11D—11D in the direction 11E in FIG. 5.

In an experiment conducted by the inventors, two enclosures 100 substantially as illustrated in FIGS. 9 and 10, were employed. The elements of enclosure 100 are similar to those described in connection with FIGS. 5–8 and 11A–11E and the same reference numerals are employed as appropriate.

Two estradiol transdermal patches 102 (Estraderm 0.1 Ciba Pharmaceutical Co.) were disposed on the back surfaces of each of surfaces 64 and 74 of the enclosure and maintained in direct contact with the hair and skin surfaces of the animal's ear. Each 20 square cm. patch contained 8 mg of Estradiol USP and 0.6 ml alcohol USP. The inactive components of the patches includes hydroxypropyl cellulose, ethylene vinyl-acetate copolymer, light mineral oil, polyisobutylene and polyethylene terephthalate.

Each pair of enclosures was applied to the untreated, (i.e. uncleaned, uncleansed and unshaved) right ears of two male Holstein calves aged 2-3 months and each weighing about 60-80 Kg. The enclosures were kept on the ears for seven consecutive days.

Thirteen venous blood samples were taken from the jugular veins of each calf between 7 AM and 8 AM for estradiol determinations. The blood samples were taken on three consecutive days prior to application of the enclosure, on the morning just prior to application of the enclosure, for the first five consecutive days and on the seventh day that the enclosure was on the ear, and for three consecutive days following removal of the enclosure.

Three days after the last blood sample was taken, serum estradiol levels of all of the samples were assayed in duplicate by a non-extraction, solid phase 125 I radioimmunoassay. The lower limit of detection of the assay was 10 Pg/ml.

Serum estradiol levels in the samples taken from the first calf on the second day and from the second calf in the first day of enclosure presence on the ear were 36.5 and 22.5 Pg/ml respectively. In all other blood samples, the serum estradiol levels were undetectable.

The estradiol serum levels achieved in the two calves, each for one day, are similar to those achieved with the implantation of growth promoting pellets in the ears of male calves, which pellets contain 20 mg Estradiol 17 Beta and 140 mg Trenbolone Acetate (B. Hoffmann: Natural Occurrence of Steroids Hormones in Food Producing Animals. In: Anabolics in Animal Production, Ed. E. Meissonnier: Paris OIE, 1983).

EXAMPLE II

An enclosure substantially as illustrated in FIGS. 9 and 10, but without any medicament or pads, was mounted on the ear of a 12 month old Holstein heifer and remained thereon for 66 consecutive days without any indications of edema, swelling, discomfort, irritation, inflammation or hair loss. Normal ear functions and movements were maintained. The heifer was kept in a pen with other heifers under normal conditions.

It will be appreciated by persons skilled in the art that the present invention is not limited by what has been particularly shown and described hereinabove. Rather the scope of the invention is defined only by the claims which follow:

We claim:

1. A technique for administering medicaments in veterinary applications comprising the steps of:

non-invasively and non-adhesively applying a medicament transdermally to a non-human animal; and non-surgically terminating the application of the medicament at a pre-determined time.

2. Method according to claim 1 and wherein said medicament is a growth promoter.

3. Method according to any of claim 1 and wherein said medicament is a fertility controlling drug.

4. Method according to any of claim 1 and wherein said medicament is a fertility synchronization agent.

5. Method according to any of claim 1 and wherein, said medicament is a nutritional supplement.

6. Method according to any of claim 1 and wherein said medicament is an anti-inflammatory agent.

7. A technique for administering medicaments in veterinary applications comprising the steps of:

non-invasively and non-adhesively applying a medicament transdermally to a non-human animal; and non-surgically terminating the application of the medicament at least a pre-determined length of time before slaughter of the animal.

8. A technique for administering medicaments in veterinary applications wherein the medicament is an agent for the control of ovulation in breeding animals and steps of applying the medicaments comprise the steps of:

non-invasively and non-adhesively applying a medicament transdermally to the ears of animals in a herd; and non-surgically terminating the application of the medicament at preselected times which are synchronized for a herd.

* * * * *